US006764583B2

(12) United States Patent
Miles

(10) Patent No.: US 6,764,583 B2
(45) Date of Patent: Jul. 20, 2004

(54) USING IMPEDANCE MEASUREMENTS FOR DETECTING PATHOGENS TRAPPED IN AN ELECTRIC FIELD

(75) Inventor: Robin R. Miles, Danville, CA (US)

(73) Assignee: The Regents of the University of California, Oakland, CA (US)

( * ) Notice: Subject to any disclaimer, the term of this patent is extended or adjusted under 35 U.S.C. 154(b) by 597 days.

(21) Appl. No.: 09/738,927

(22) Filed: Dec. 13, 2000

(65) Prior Publication Data

US 2002/0070114 A1 Jun. 13, 2002

(51) Int. Cl.[7] ................ G01N 27/26; G01N 27/447; C25B 11/02
(52) U.S. Cl. ................ 204/452; 204/461; 204/400; 204/403.01; 435/287.2; 435/287.1; 436/806
(58) Field of Search .............. 204/452, 461, 204/400, 403.01, 403; 435/287.2, 287.1; 436/806

(56) References Cited

U.S. PATENT DOCUMENTS

| | | | |
|---|---|---|---|
| 4,326,934 A | 4/1982 | Pohl | 204/180 R |
| 5,344,535 A | 9/1994 | Betts et al. | 204/183.1 |
| 5,413,686 A | 5/1995 | Klein et al. | 204/299 R |
| 5,489,506 A | 2/1996 | Crane | 435/2 |
| 5,567,301 A * | 10/1996 | Stetter et al. | 205/777.5 |
| 5,569,367 A | 10/1996 | Betts et al. | 204/547 |
| 5,814,200 A | 9/1998 | Pethig et al. | 204/547 |
| 5,858,192 A | 1/1999 | Becker et al. | 204/547 |
| 5,888,370 A | 3/1999 | Becker et al. | 204/643 |
| 2001/0053535 A1 * | 12/2001 | Bashir et al. | 435/34 |
| 2002/0072054 A1 * | 6/2002 | Miles et al. | 435/6 |
| 2002/0076690 A1 * | 6/2002 | Miles et al. | 435/5 |
| 2002/0150886 A1 * | 10/2002 | Miles et al. | 435/5 |

FOREIGN PATENT DOCUMENTS

WO  WO 97/21094 A1 *  6/1997

OTHER PUBLICATIONS

Milner et al, "Dielectrophoretic classification of bacteria using differential impedance measurements," Electronics Letters, vol. 34, No. 1, Jan. 8, 1998.*
Fiedler, S., et al., "Dielectrophoretic Sorting of Particles and Cells in a Microsystem," Anal. Chem, 1998, 70, American Chemical Society, pp. 1909–1915.
Green, N. G., et al., "Separation of submicrometre particles using a combination of dielectrophoretic and electrohydrodynamic forces," J. Phys. D: Appl. Phys. 31, 1998, IOP Publishing Ltd., pp. L25–L30.
Suehiro, J., et al., "The dielectrophoretic movement and positioning of biological cell using a three-dimensional grid electrode system," J. Phys. D: Appl. Phys. 31, 1998, IOP Publishing Ltd., pp. 3298–3305.

* cited by examiner

Primary Examiner—Alan Diamond
(74) Attorney, Agent, or Firm—Eddie E. Scott; L. E. Carnahan; Alan H. Thompson

(57) ABSTRACT

Impedance measurements between the electrodes in an electric field is utilized to detect the presence of pathogens trapped in the electric field. Since particles trapped in a field using the dielectiphoretic force changes the impedance between the electrodes by changing the dielectric material between the electrodes, the degree of particle trapping can be determined by measuring the impedance. This measurement is used to determine if sufficient pathogen have been collected to analyze further or potentially to identify the pathogen.

11 Claims, 2 Drawing Sheets

USING IMPEDANCE MEASUREMENTS FOR DETECTING PATHOGENS TRAPPED IN AN ELECTRIC FIELD

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to the collection or concentration of particles in an electric field of fluidic device, particularly to detecting the presence of pathogens trapped in an electric field, and more particularly to the use of impedance measurements to detect the presence of pathogens trapped in an electric field.

Dielectrophoresis (DEP) is the electrokinetic motion of dielectrically polarized particles in non-uniform electrical fields and is currently an active area of research. Because most biological cells and macromolecules behave as dielectric particles in external AC electric fields, DEP has found many useful biotechnological applications including separation, levitation, and characterization of biological particles. The use of dielectrophoresis to collect particles is well known when operating under pressure driven flow. Currently efforts are being carried out involving concentrating bacterial biological sample for DNA analysis on sets of interdigitated electrodes using the dielectrophoretic force generated for a particle in the non-uniform field generated by applying a voltage to the electrodes.

There has been a need for a means for detecting the presence of pathogens at the electrodes to determine if sufficient pathogens have been collected to analyze further or potentially to identify the pathogen.

The present invention provides a solution to the above mentioned need by using impedance measurments between the electrodes to detect the presence of pathogens trapped in an electric field generated by the electrodes. Due to the change of impedance between the electrodes which is caused by trapped pathogens, the impedance change is used to determine the degree of particle trapping. Thus the invention provides an impedance sensor for detecting pathogens.

SUMMARY OF THE INVENTION

It is an object of the present invention to determine the presence of pathogens trapped in an electric field.

A further object of the invention is to use impedance measurements between electrodes to determine the degree of pathogen trapping in an electric field.

A further object of the invention is to provide a sensor to detect particles trapped in an electric field using the dielectrophoretic force.

Another object of the invention is to provide a method and apparatus for detecting pathogens trapped in a field using the dielectrophoretic force by measuring changes in the impedance between the electrodes caused by the trapped pathogens.

Another object of the invention is to provide a sensor used to detect the presence of pathogens on electrodes used to concentrate sample using the dielectrophoretic force or any other force on a surface by impedance measurements between the electrodes.

Other objects and advantages will become apparent from the following description and accompanying drawings.

Basically the present invention involves an apparatus and method for detecting the presence of pathogens trapped on electrodes by impedance measurements. Since the presence of pathogens trapped on electrodes, such as by the electrophoretic force, the impedance between the electrodes changes as the number of trapped pathogens increases, and this change of impedance is utilized to determine if sufficient pathogen has been collected to analyze further or potentially to identify the pathogen. The apparatus merely involves interdigitated electrodes, for example, located on the inner surface of a fluidic channel through which sample is passed and pathogens are trapped by the dielectrophoretic force, as known in the art, and a means for measuring the impedance between the electrodes, which changes by the trapping of the pathogens. By determining the impendance change, the amount of trapped pathogen can be determined. Thus, the invention involves a sensor using impedance change to detect the presence of pathogens trapped in an electric field produced by the interdigitated electrodes, via an AC voltage applied across the interdigitaled electrodes. The sensor can effectively detect trapped pathogens when the sample is passed through the fluidic channel by pressure driven flow or by electrokinetic/electroosmotic flow, etc. Thus, any commercial assay such as clinical PCR or any biological research apparatus that is concentrating sample can utilize the sensor of the present invention to determine if sufficient DNA, pathogens, etc., have been collected to analyze some or to identify the pathogen.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

The present invention is directed to the use of impedance measurements to detect the presence of pathogens trapped in an electric field. Particles trapped in an electric field using the dielectrophoretic force change the impendance between the electrodes by changing the dielectric material between the electrodes. This impedance is measured to determine the degree of particle trapping. This measure is used to determine if sufficient pathogen has been collected to analyze further or potentially to identify the pathogen.

A fluidic channel is provided with interdigitatd electrodes patterned on an inner surface of the channel. An AC voltage is applied across the interdigitaled electrodes and particles passing through the channel are trapped by the dielectrophoretic force generated for a particle in the non-uniform field generated by the electrodes. A sensor is provided for measuring the impedance across the electrodes, and as the particles are trapped the impedance changes. By measuring the impedance between the interdigitated electrodes, one can track how much bacteria (particles, pathogens, etc.) has been collected. The bacteria replaces the fluid in the electric field between the two electrodes, changing the dielectric constant of the media between the electrode plates. This is picked up by the sensor as a change in impedance.

As known in the art, biological particles are attracted to areas of high field gradient due to the dielectrophoretic force resulting from the dipole induced in the particle by the field. This field is being used to trap particles, and/or DNA, from a stream of sample fluid for later analysis. This same field is used to measure the impedance between the electrodes. As the particle cuts the electrical field lines, it changes the dietric constant been the electrodes, and thus the impedance. By measuring the impedance change one can determine how many particles have been trapped. Thus, one can determine when to release the particles for further sample preparation.

Figure 1:
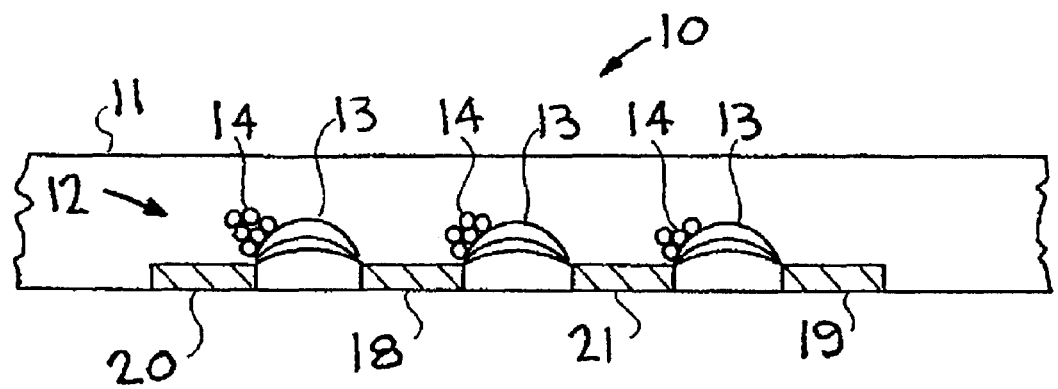
FIG. 1 illustrates a cross-section of a fluidic channel with patterned interdigitated electrodes positioned along a length thereof.
Figure 2:
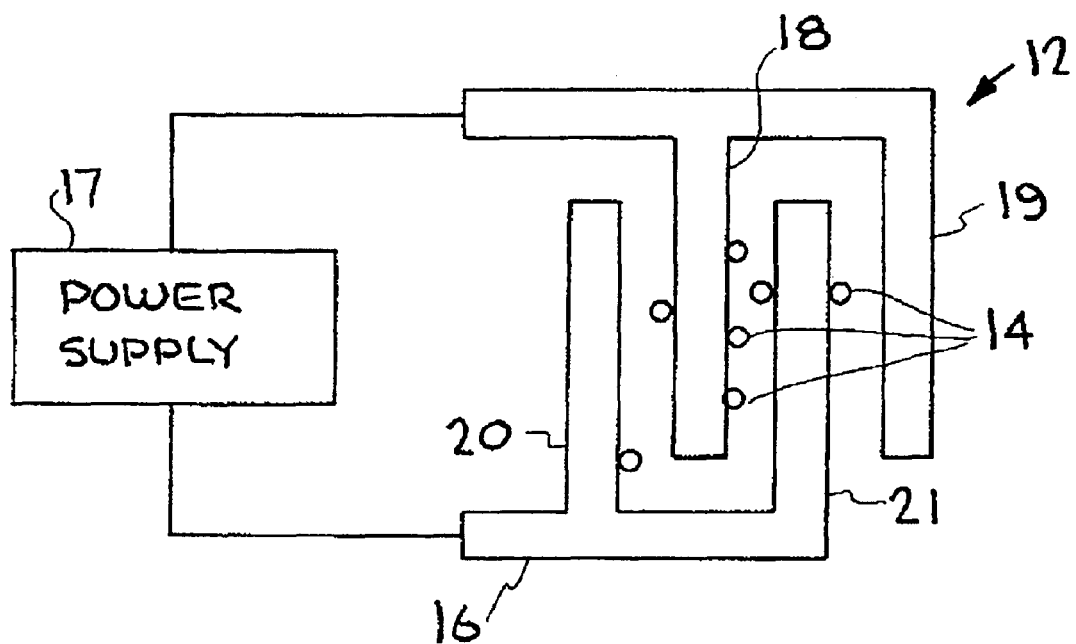
FIG. 2 is a top view of patterned interdigitated electrode of FIG. 1.
Figure 3:
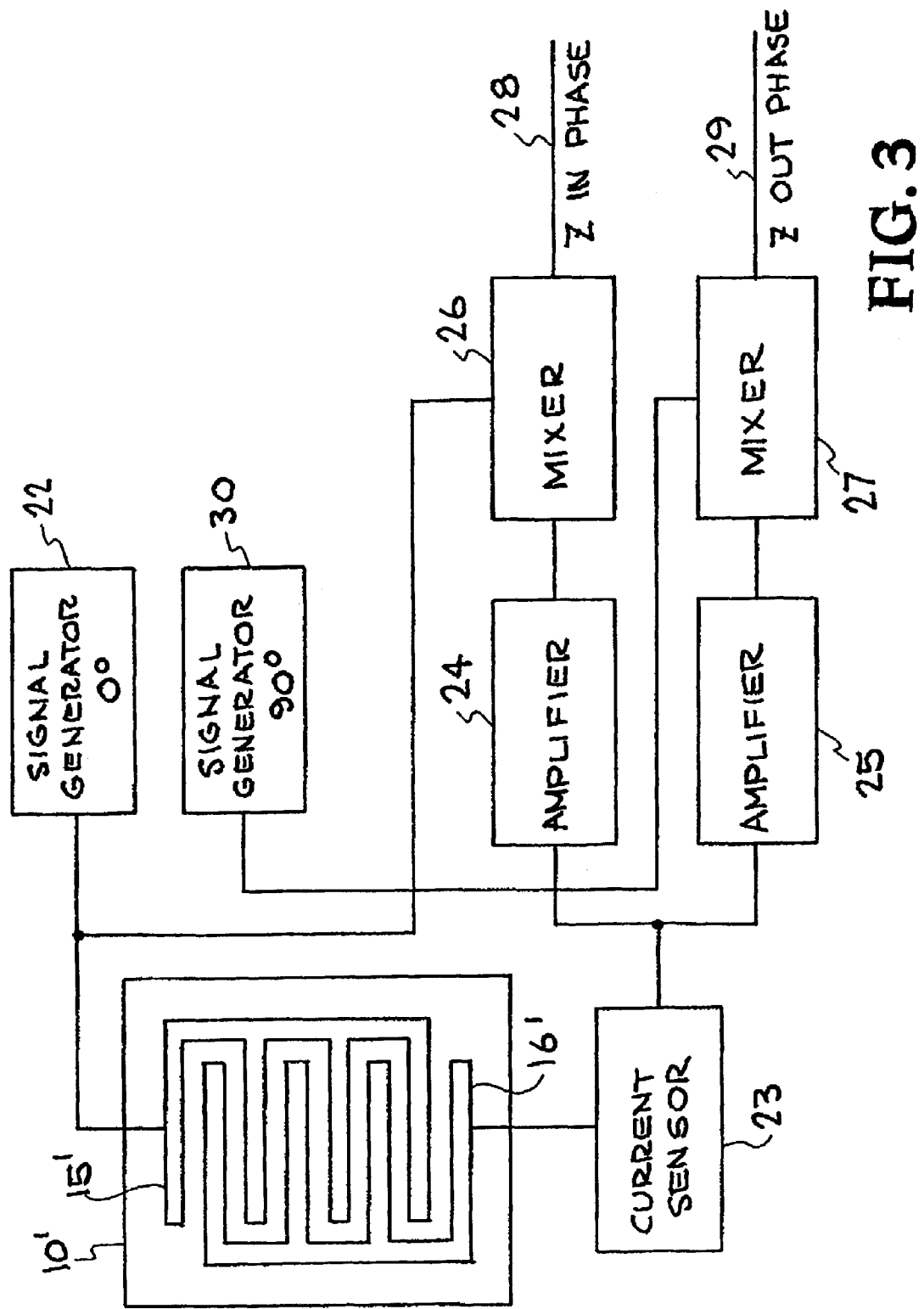
FIG. 3 schematically illustrate an embodiment of an impedance sensor for caring out the invention.

Referring now to the drawings, FIG. 1 illustrates a fluidic channel, which may be a single channel device or one of many channels in a microfluidic device, with patterned interdigitated electrodes, as shown greatly enlarged in FIG. 2. A sensor, shown in FIG. 3, is apperatively connected to each of the interdigitated electrodes to measure the impedance and impedance change in the electrodes as particles are trapped (see FIG. 2) in the electric field as shown in FIG. 1. The sensor may be of a continuously activated or periodically activated type.

As illustrated in FIG. 1, the fluidic device 10 includes a fluidic channel 11, which may be one of a number of microfluidic channels through which a sample fluid passes by pressure driven flow or by electrokinetic/electroosmotic flow. The channel 11 may be formed, for example, in a pair of bonded glass plates. Patterned in an inner surface of the channel 11 are interdigitated electrodes 12 (see FIG. 2) which produce an electric field 13 causing trapping, collection, or concentration of particle 14 of the fluid flowing through the channel 11.

FIG. 2 illustrates an enlarged top view of an embodiment of the interdigitated electrodes 12 of FIG. 1, wherein the electrode 12 comprises a pair of electrode plates 15 and 16, each electrically connected to an AC power source 17. Each electrode plate 15 and 16 has a pair of legs 18–19 and 20–21, respectively, with leg 18 of electrode plate 15 being located intermediate legs 20 and 21 of electrode plate 16. Particles 14 are trapped on the legs of the electrode plates 15 and 16 by the electric field 13 produced by the AC voltage applied across the electrode plates 15 and 16.

As can be seen in FIG. 2, as the particles 14 collect on the legs of the electrode plates 15 and 16, they cause a change in the dielectric constant between the electrodes, and thus a change in the impedance between the electrodes. By measuring the change in impedance it can be determined how many particles have been trapped. This measure can be used to determine if sufficient particles, pathogen, DNA, etc. has been collected to enable further analyzing thereof or potentially used to identify the pathogen. Each of the interdigitated electrodes 12 are connected to a sensor unit of FIG. 3.

FIG. 3 schematically illustrates an embodiment of an impedance sensor for measuring change in the impedance between electrode plates 15 and 16 of FIG. 2 due to the trapping of particles 14 via the interdigitated electrode legs 18–19 and 20–21. As shown the impedance sensor is operatively connected to electrodes 15' and 16' located in a microchannel device 10', with a 0° signal generator 22 electrically connected to electrode 15' and a current sensor 23 electrically connected to electrode 16'. A pair of amplifiers 24 and 25 are connected in parallel to current sensor 23, with mixers 26 and 27 operatively connected to amplifiers 24 and 25, which measure the impedance (z) in phase, indicated at 28, and out-of-phase indicated at 29, of the components of the device. A 90° signal generator 30 is electrically connected to the mixer 27, with signal generator 22 electrically connected to mixer 26. Signal generators 22 and 30 drive dielectrophoretic device electrodes 15' and 16'. Collected particles cause a change in the device impedance, as described above, and the output of the current sensor 23. Amplifiers 24 and 25 and mixers 26 and 27 measure the in-phase 28 and out-of-phase 29 components of the devices complex impedance.

It has thus been shown that the present invention provides a method and apparatus which utilizes impedance measurements to sense or detect the presence of pathogens trapped in an electric field. The sensor of this invention can be used in any research or commercial assay, such as clinical PCR, wherein concentrating of sample particles or DNA is carried out. Also, the sensor can be used, for example, in counter biological warfare detectors to detect the presence of pathogens on electrodes used to concentrate sample using the dielectrophoretic force or any other force one a surface.

While particular embodiments of the interdigitaled electrodes and the sensor have been illustrated and described to exemplify and teach the principles of the invention, such are not intended to be limiting. Modifications and changes may become apparent to those skilled in the art, and it is intended that the invention be limited only by the scope of the appended claims.

The invention claimed is:

1. A device for detecting the presence of pathogens trapped in an electric field, comprising
   a fluidic channel through which a fluid carrying said pathogens flows, said fluidic channel having a surface,
   at least one pair of interdigitated electrodes positioned on said surface of said fluidic channel with a space between said interdigitated electrodes,
   said at least one pair of interdigitated electrodes localized along said fluidic channel, with said at least one pair being located on the same surface of said fluidic channel, said interdigitated electrodes having electrode plates with a surface,
   an AC power source for applying a voltage across said electrode plates of said at least one pair interdigitated electrodes for producing an electric field to enable trapping of pathogens passing through said fluidic channel, and
   means for measuring the impedance between said electrode plates for determining the presence of trapped pathogens.

2. The device of claim 1, additionally including a plurality of spaced interdigitated electrodes located along a length of the fluidic channel.

3. The device of claim 2, wherein each of said interdigitated electrodes is provided with a means for measuring the impedance thereof.

4. The device of claim 2, wherein said means for measuring the impedance is operatively connected to each of said electrode plates of the spaced interdigitated electrodes.

5. The device of claim 1, wherein said electrode plates have at least one leg located in spaced relation to at least one leg of another of the pair of plates.

6. The device of claim 5, wherein each of said electrode plates includes a pair of space leg sections each of said leg section of one of said electrode plates being located adjacent to a leg section of another of said electrode plates.

7. The device of claim 1, wherein said means for measuring the impedance, comprises: a plurality of signal generators, a current sensor, a plurality of amplifiers, and a plurality of mixers to measure in-phase and out-of-phase components of impedance between said electrode plates.

8. In a device for trapping particles in an electric field formed by electrodes the improvement comprising:
- a fluidic channel through which a fluid carrying said particles flows, said fluidic channel having a surface,
- at least one pair of interdigitated electrodes positioned on said surface of said fluidic channel with a space between said interdigitated electrodes,
- said at least one pair of interdigitated electrodes localized along said fluidic channel, with said at least one pair being located on the same surface of said fluidic channel, said interdigitated electrodes having electrode plates with a surface,
- means for detecting the presence of trapped particles,
- said means including means for the detection of impedance changes between said electrode plates.

9. The improvement of claim 8, wherein said means comprises a sensor for measuring impedance change between said electrodes.

10. The improvement of claim 9, wherein said sensor is operatively connected to said plates.

11. The improvement of claim 9, wherein said sensor comprises: a pair of signal generators, a current sensor connected to one of said electrodes, a pair of parallel connected amplifier/mixer assemblies operatively connected to said current sensor, said pair of signal generators being operatively connected to a mixer of said amplifier/mixer assemblies, with one of said pair of signal generators being also operatively connected to another electrode.

* * * * *